(12) United States Patent
Wall

(10) Patent No.: US 11,751,920 B2
(45) Date of Patent: Sep. 12, 2023

(54) SURGICAL INSTRUMENT AND METHOD

(71) Applicant: WARSAW ORTHOPEDIC INC., Warsaw, IN (US)

(72) Inventor: Daniel Paxton Wall, Cordova, TX (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/527,485

(22) Filed: Nov. 16, 2021

(65) Prior Publication Data

US 2023/0149055 A1 May 18, 2023

(51) Int. Cl.
*A61B 17/70* (2006.01)
(52) U.S. Cl.
CPC ...... *A61B 17/7082* (2013.01); *A61B 17/7035* (2013.01)
(58) Field of Classification Search
None
See application file for complete search history.

(56) References Cited

U.S. PATENT DOCUMENTS

| 10,448,978 | B2 | 10/2019 | Wall et al. | |
|---|---|---|---|---|
| 2015/0282855 | A1* | 10/2015 | Bess | A61B 17/7082 606/86 A |
| 2016/0262809 | A1* | 9/2016 | May | A61B 17/7082 |
| 2018/0303522 | A1 | 10/2018 | Wall et al. | |
| 2019/0029736 | A1 | 1/2019 | Wall et al. | |
| 2020/0390478 | A1* | 12/2020 | Rodriguez | A61B 17/7001 |
| 2020/0390486 | A1* | 12/2020 | Rodriguez | A61B 17/8886 |
| 2021/0228244 | A1* | 7/2021 | Wall | A61B 17/8872 |
| 2021/0228280 | A1* | 7/2021 | Wall | A61B 17/1697 |

* cited by examiner

*Primary Examiner* — Tessa M Matthews
(74) *Attorney, Agent, or Firm* — Sorell, Lenna & Schmidt, LLP

(57) ABSTRACT

A surgical instrument includes a first member. A second member is disposable with the first member and includes an inner surface. An actuator defines a cavity and is releasably connectable with the first member. A third member is engageable with the inner surface. The first member and the second member are translatable relative to the actuator. Systems, spinal constructs, implants and methods are disclosed.

20 Claims, 11 Drawing Sheets

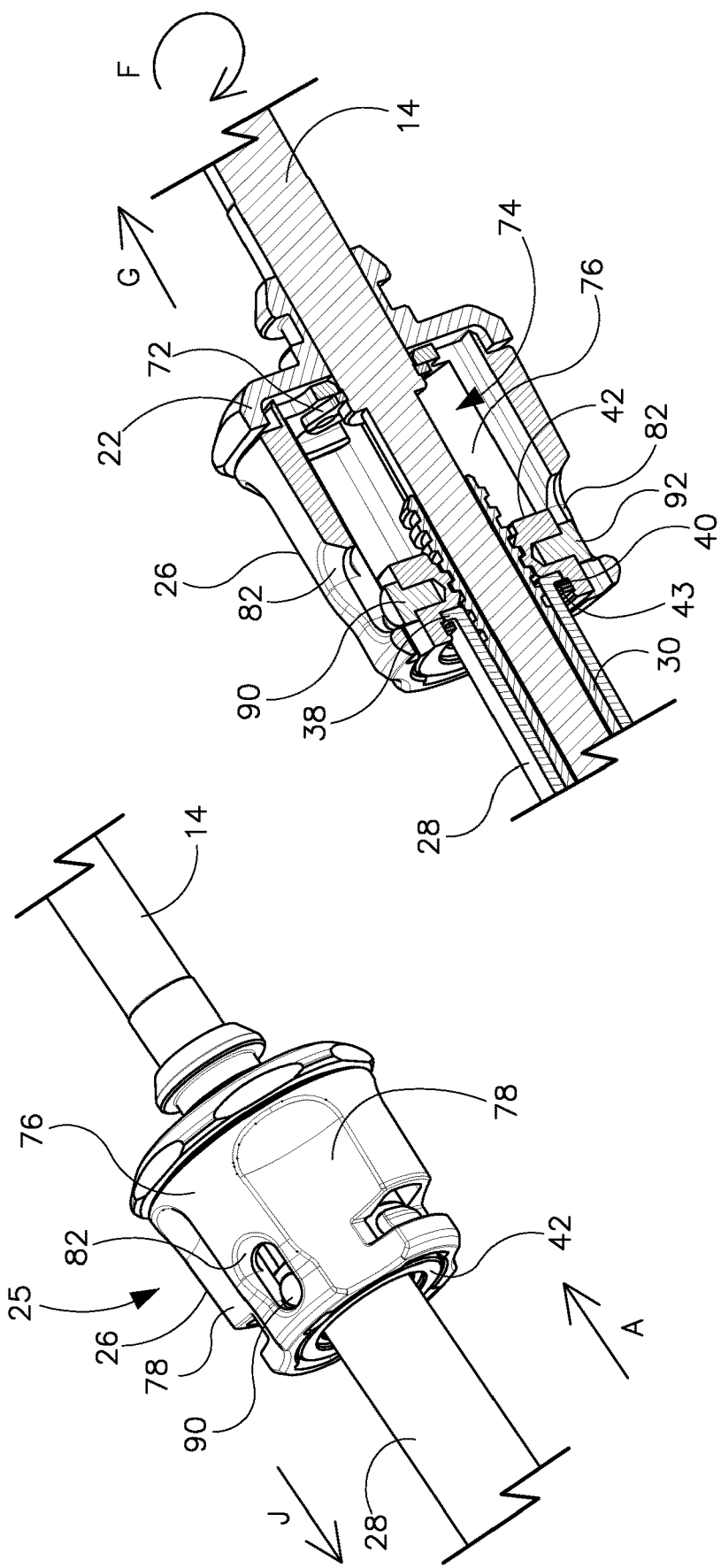

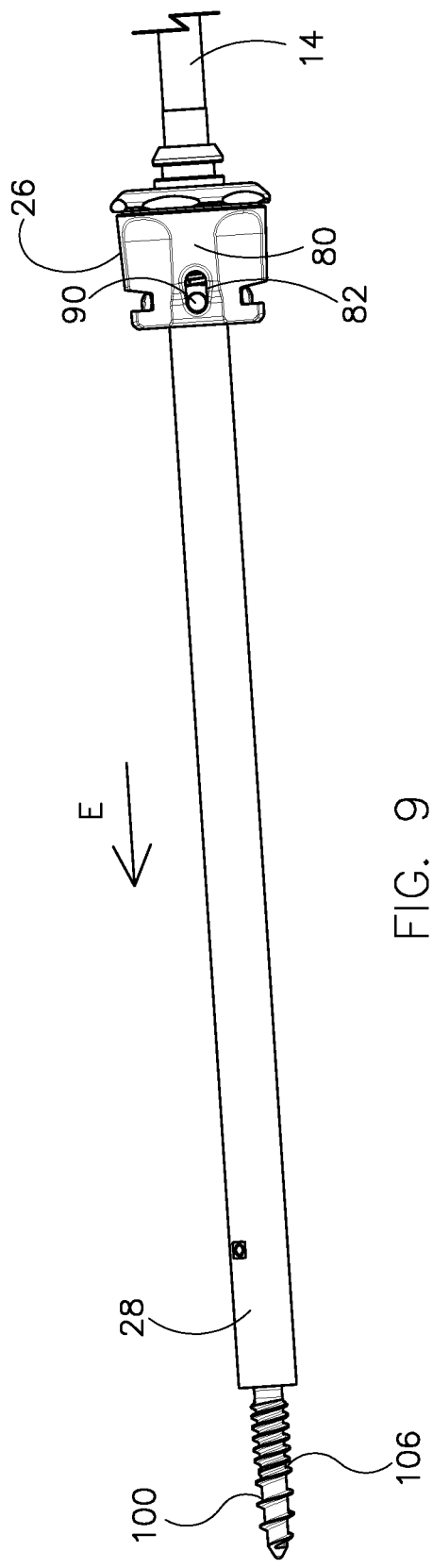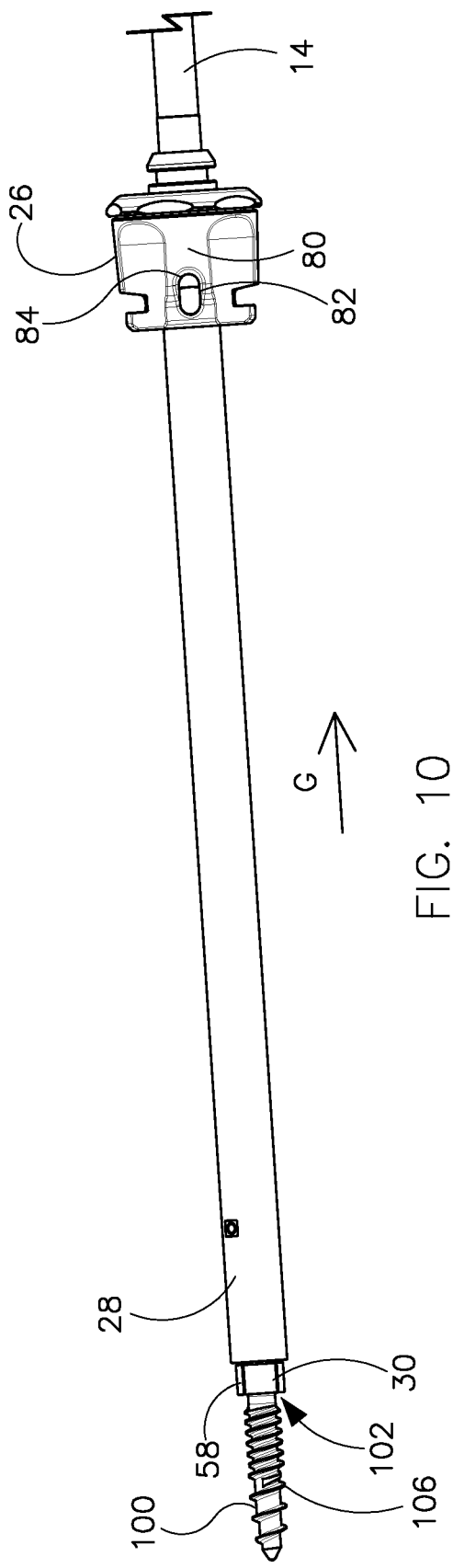

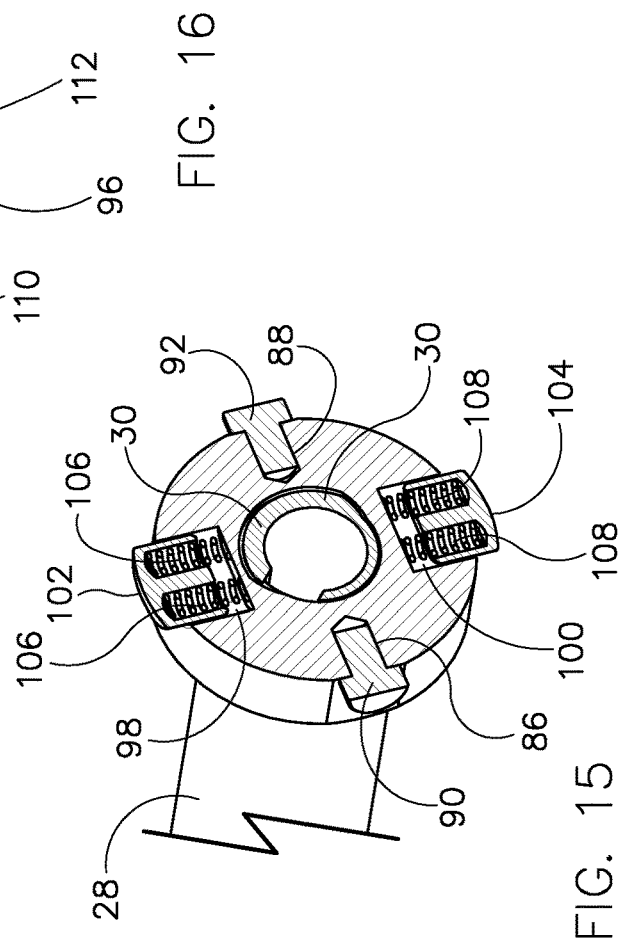
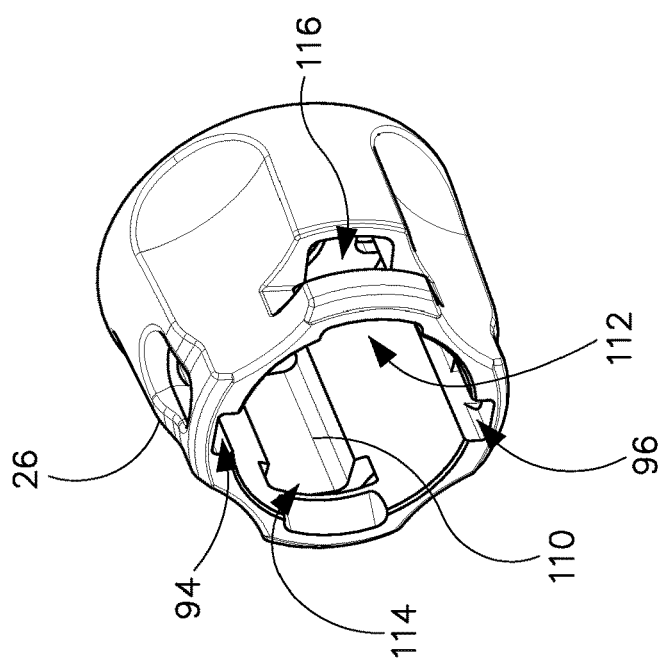
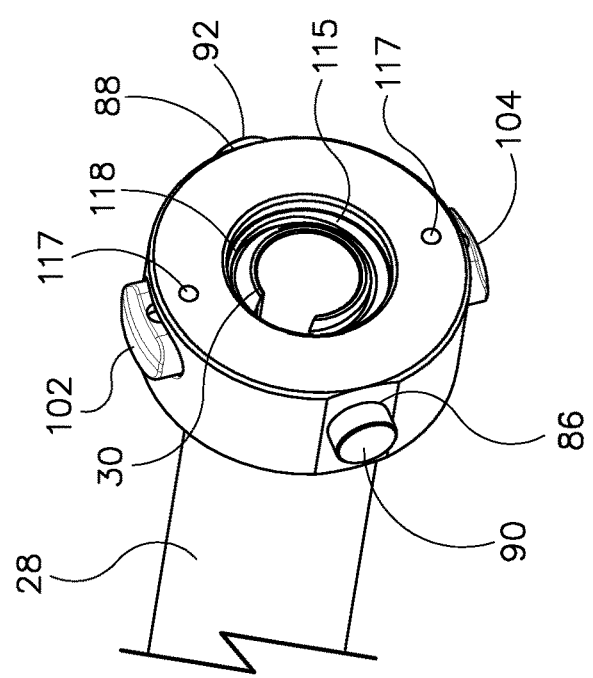

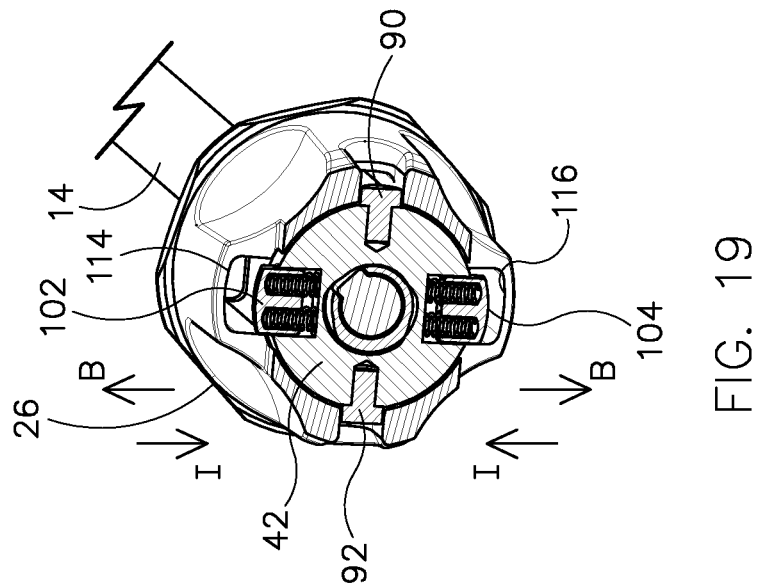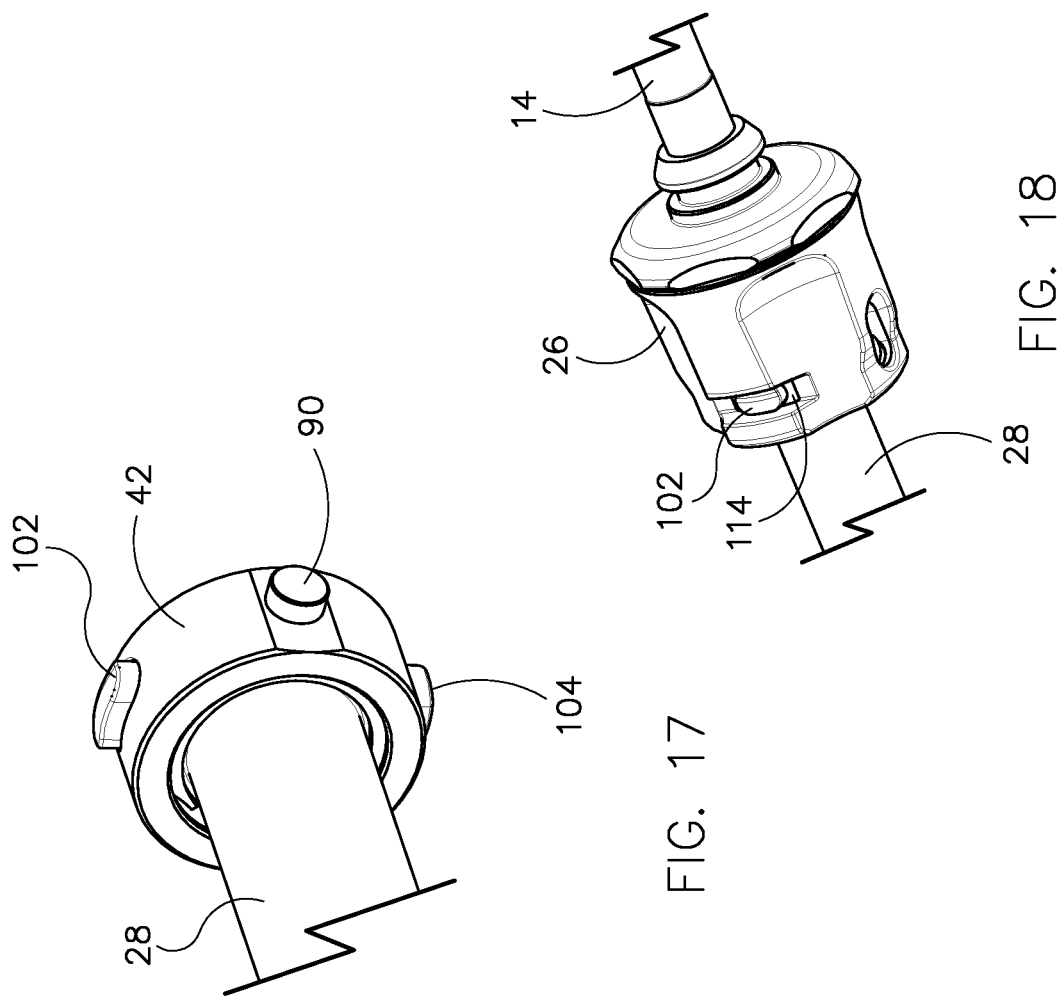

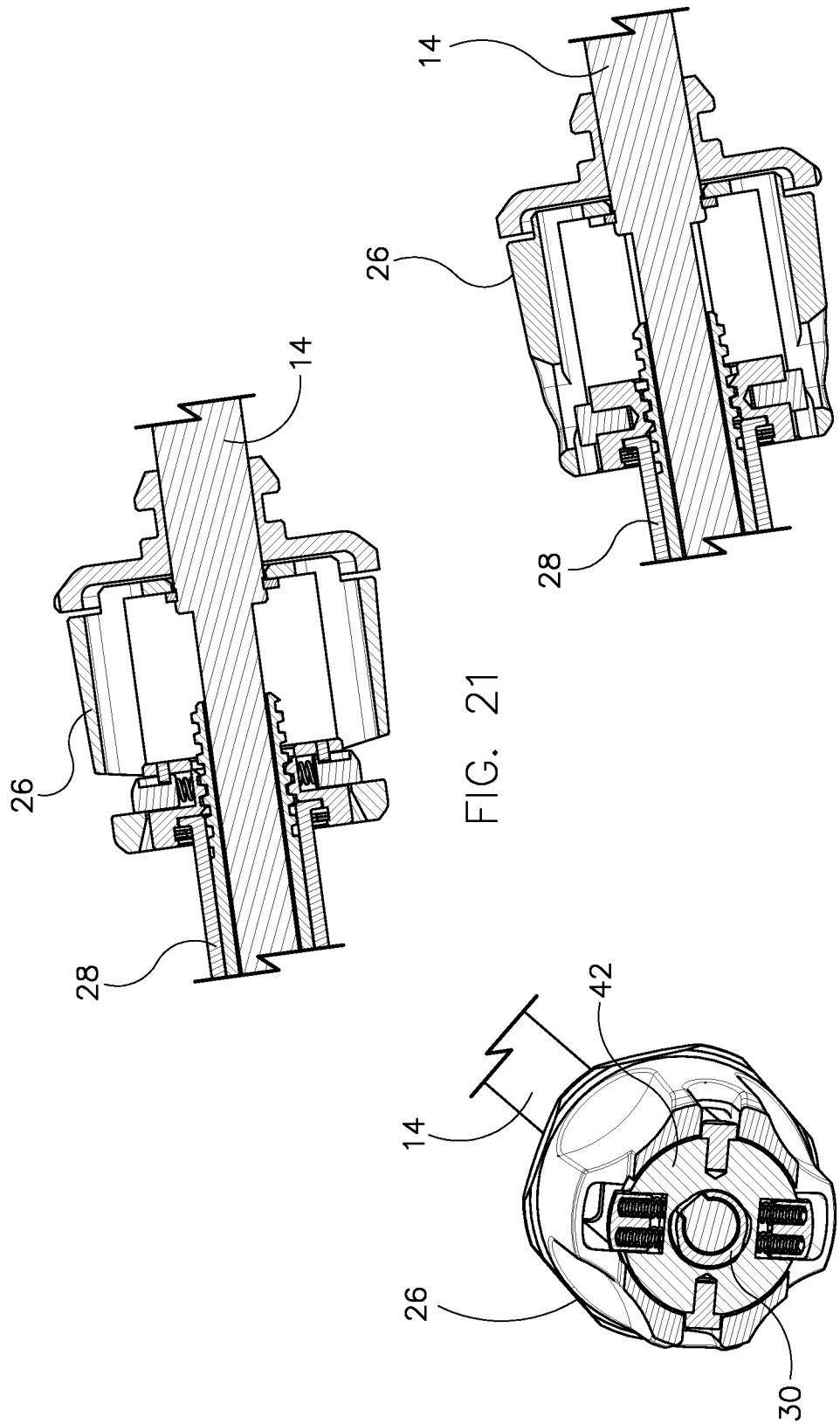

US 11,751,920 B2

SURGICAL INSTRUMENT AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal implants such as vertebral rods and/or fasteners are often used to provide stability to a treated region. Rods redirect stresses away from a damaged or defective region while healing takes place to restore proper alignment and generally support vertebral members. During surgical treatment, spinal implants can be delivered to a surgical site, for example, so that the rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument includes a first member. A second member is disposable with the first member and includes an inner surface. An actuator defines a cavity and is releasably connectable with the first member. A third member is engageable with the inner surface. The first member and the second member are translatable relative to the actuator. In some embodiments, systems, spinal constructs, implants and methods are disclosed.

In some embodiments, the surgical instrument includes an outer sleeve. An inner sleeve is disposable with the outer sleeve and includes an inner surface. An actuator includes a rotatable knob and a collar. The collar is releasably connectable with the outer sleeve. An inner shaft is engageable with the inner surface of the inner sleeve. The outer sleeve is translatable relative to the knob. The inner sleeve is translatable relative to the collar.

In some embodiments, the surgical instrument includes a first member including an end having a rim. A second member is disposable with the first member and includes an inner surface. An actuator includes a knob and a collar. The collar is engageable with the rim and the knob is releasably connectable with the first member. A third member is engageable with the inner surface and includes a drive. The first member is translatable relative to the knob. The second member is translatable relative to the collar. The drive of the third member being engageable with a socket of a bone fastener head.

BRIEF DESCRIPTION OF THE DRAWINGS

The present disclosure will become more readily apparent from the specific description accompanied by the following drawings, in which:

FIG. 5 is a break away view of components of the surgical system shown in FIG. 1;

FIG. 6 is a cross section view of the components shown in FIG. 5;

FIG. 9 is a break away view of components of the surgical system shown in FIG. 1;

FIG. 10 is a break away view of components of the surgical system shown in FIG. 1;

FIG. 14 is a break away view of components of the surgical system shown in FIG. 1;

FIG. 15 is a cross section view of components of the surgical system shown in FIG. 14;

FIG. 16 is a component of the surgical system shown in FIG. 1;

FIG. 17 is a break away view of components of the surgical system shown in FIG. 1;

FIG. 18 is a break away view of components of the surgical system shown in FIG. 1;

FIG. 19 is a cross section view of components of the surgical system shown in FIG. 18;

FIG. 20 is a cross section view of components of the surgical system shown in FIG. 18;

FIG. 21 is a cross section view of components of the surgical system shown in FIG. 18;

FIG. 22 is a cross section view of components of the surgical system shown in FIG. 18;

DETAILED DESCRIPTION

Figure 1:
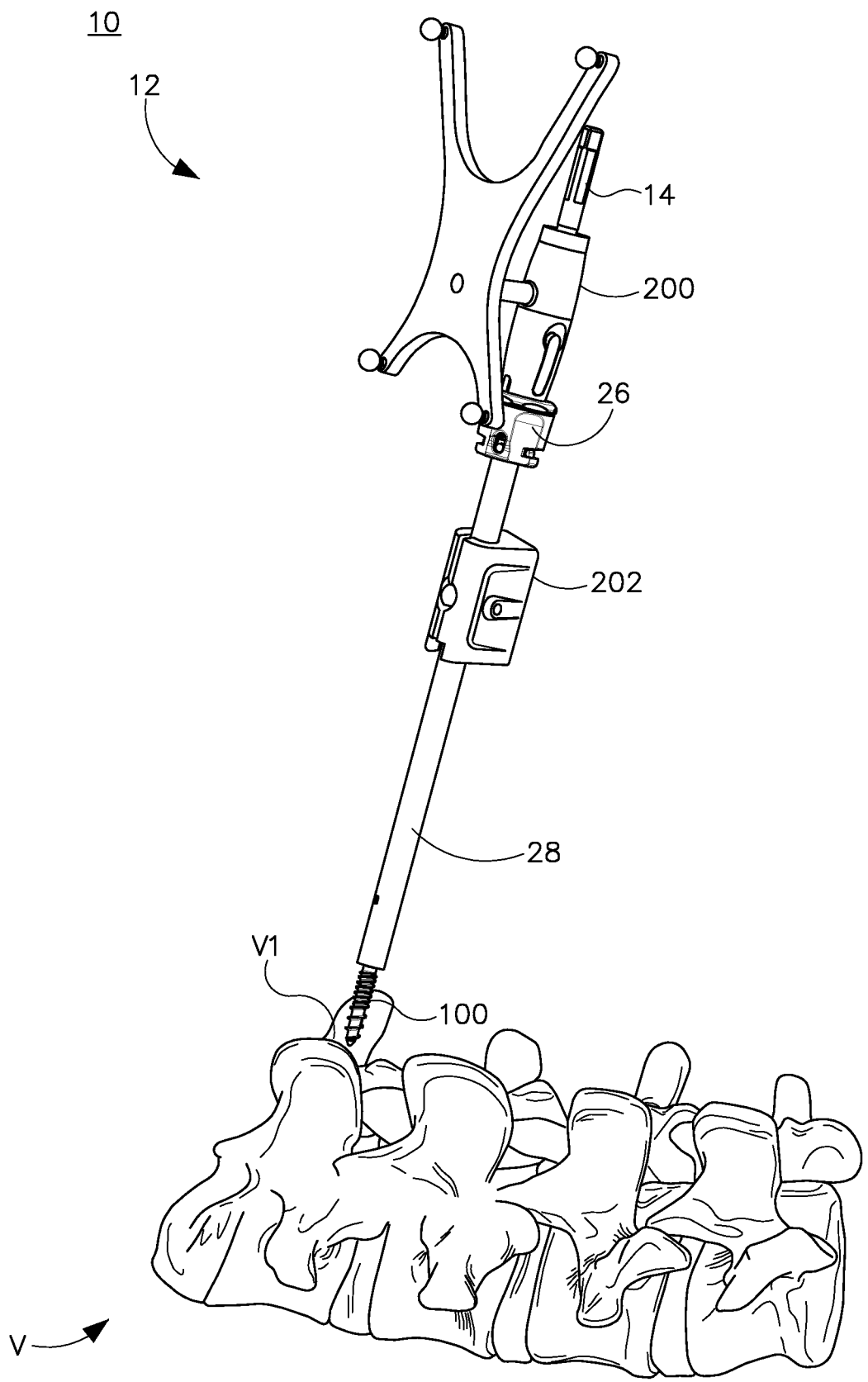
FIG. 1 is a perspective view of components of one embodiment of a surgical system in accordance with the principles of the present disclosure disposed with vertebrae.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a surgical instrument including a surgical driver configured for connection with selected ranges of bone fasteners, for example, screws for use with surgical robotic systems. In some embodiments, the surgical driver defines a selected length. In some embodiments, the length, for example, a bucket length, includes a distance between a selected portion of a shaft of the surgical driver and a distal end of an outer sleeve of the surgical driver. In some embodiments, the surgical driver includes an actuator, for example, a knob. In some embodiments, the bucket length is configured to be shortened via translation of the outer sleeve within the knob. In some embodiments, the bucket length is shortened such that the surgical driver includes a bucket length range of about 150 millimeters (mm) to 300 mm. In some embodiments, the bucket length range is about 201 mm to 260 mm. In some embodiments, the bucket length is configured to be shortened via translation of the outer sleeve within the knob such that the surgical driver is compatible for connection with bone screw lengths in a range of about 25 mm to 150 mm. In some embodiments, the surgical driver is configured for use in procedures, for example, adult deformity procedures.

In some embodiments, the present surgical system includes a surgical driver configured for use in surgical navigation. In some embodiments, the surgical navigation includes robotic and/or navigation guidance. In some embodiments, the surgical driver includes an actuator, for example, a knob and a collar. In some embodiments, the collar is slidably engageable with an inner surface of the knob. In some embodiments, the collar is configured for engagement with an outer sleeve to translate the outer sleeve relative to the knob. In some embodiments, an inner sleeve is configured for disposal with the outer sleeve. In some embodiments, the outer sleeve and the inner sleeve are detachable from the surgical driver via the collar. In some embodiments, the outer sleeve is disposed in a releasable connection with the knob via the collar. In some embodiments, the knob is translationally fixed to a shaft of the surgical driver. In some embodiments, the outer sleeve translates within the knob via the collar and the knob does not translate within an inner surface of the sleeve. In some embodiments, translation of the outer sleeve within the knob enables a decrease in bucket length. In some embodiments, the knob includes recesses configured to accommodate an assembly and/or dis-assembly of the device. In some embodiments, the knob includes recesses, for example, four thumb recesses. In some embodiments, the knob is acorn shaped.

In some embodiments, the present surgical system includes a surgical driver. In some embodiments, the surgical driver includes a shaft, an actuator including a knob and collar, an outer sleeve, an inner sleeve and a navigation locking component including a bushing lock. In some embodiments, the surgical driver is configured for connection with a shank of a screw. In some embodiments, the knob does not translate relative to the bushing to release the shank of the screw. In some embodiments, the bushing is fixed to the shaft. In some embodiments, the bushing extends to an end that includes a flange. In some embodiments, the flange is configured to engage an end of the knob to prevent unintentional loosening of the knob during use. In some embodiments, the flange includes a thread.

In some embodiments, the present surgical system includes a surgical driver that includes an actuator, for example, a knob and a collar. In some embodiments, the collar is configured for disposal within the knob and is configured for engagement with an outer sleeve of the driver. In some embodiments, the collar includes an engagement indicator configured to indicate translation of the outer sleeve within the knob. In some embodiments, the collar includes a pair of pins fixed to the collar. In some embodiments, the pins include a selected color. In some embodiments, a head of each of the pins is laser marked black and/or is anodized/physical vapor deposition (PVD) coated. In some embodiments, the knob includes a pair of indicator windows. In some embodiments, each pin of the collar is viewable via each of the windows to indicate translation of the outer sleeve within the knob. In some embodiments, the pins are viewable in the windows when the outer sleeve translates in a distal direction relative to the knob and an end of the outer sleeve is disposed over a collet of an inner sleeve. In some embodiments, the pins are not viewable and the collet is fully exposed in the windows when the outer sleeve translates in a proximal direction relative to the knob. In some embodiments, the windows are tapered to increase visibility of the pins.

In some embodiments, the present surgical system includes a surgical driver including the outer sleeve and the inner sleeve that are detachable from the knob via the collar. In some embodiments, the knob includes the pair of windows each configured for viewing each of the pins. In some embodiments, the knob includes a pair of slots each configured for slidable engagement with each of the pins such that the pins are translatable. In some embodiments, the knob includes two openings. In some embodiments, a pair of spring-loaded buttons of the collar, for example, plungers, are configured for disposal with the openings. In some embodiments the spring loaded plungers are configured to prevent axial translation, releasable connection and facilitate disengagement of the outer sleeve with the knob. In some embodiments, each spring includes a force of about 0.5 to 1.5 pound force (lbf) at solid. In some embodiments, full depression of each of the springs includes a force of about 1 to 4 pounds (lbs) per plunger. In some embodiments, pins are configured to retain the plungers to the collar. In some embodiments, the plungers and/or the pins are laser welded. In some embodiments, the fixed pins are laser welded on an outer surface of the collar. In some embodiments, a shank is configured for disposal through an 8 to 12 mm diameter robotic arm guide of the surgical driver.

In some embodiments, the present surgical system includes a method of assembling components of a surgical driver to connect the outer sleeve including the step of aligning a keyway of each of the plungers with corresponding slots. In some embodiments, the method includes the step of aligning the pair of fixed pins with the slots in the knob and depressing the pair of plungers until the plungers engage in a snap fit with the openings.

In some embodiments, the present surgical system includes a method of disassembling components of a surgical driver to disconnect the outer sleeve from the surgical driver including the step of depressing the pair of plungers simultaneously to slide the collar out of an interior of the knob such that the outer sleeve is disconnected from the surgical driver. In some embodiments, an instrument or pusher is provided to depress the plungers due to the size of the pair of openings of the collar. In some embodiments, components of the surgical driver can be disassembled to clean the surgical driver.

In some embodiments, the present surgical system includes a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robotic guided surgical screw driver employed with robotic and/or navigation guidance, which may include an image guide.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-25, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, for example, a bone fastener, at a surgical site of a patient, which includes, for example, a spine. In some embodiments, the spinal implant can include one or more components of one or more spinal constructs, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 2:
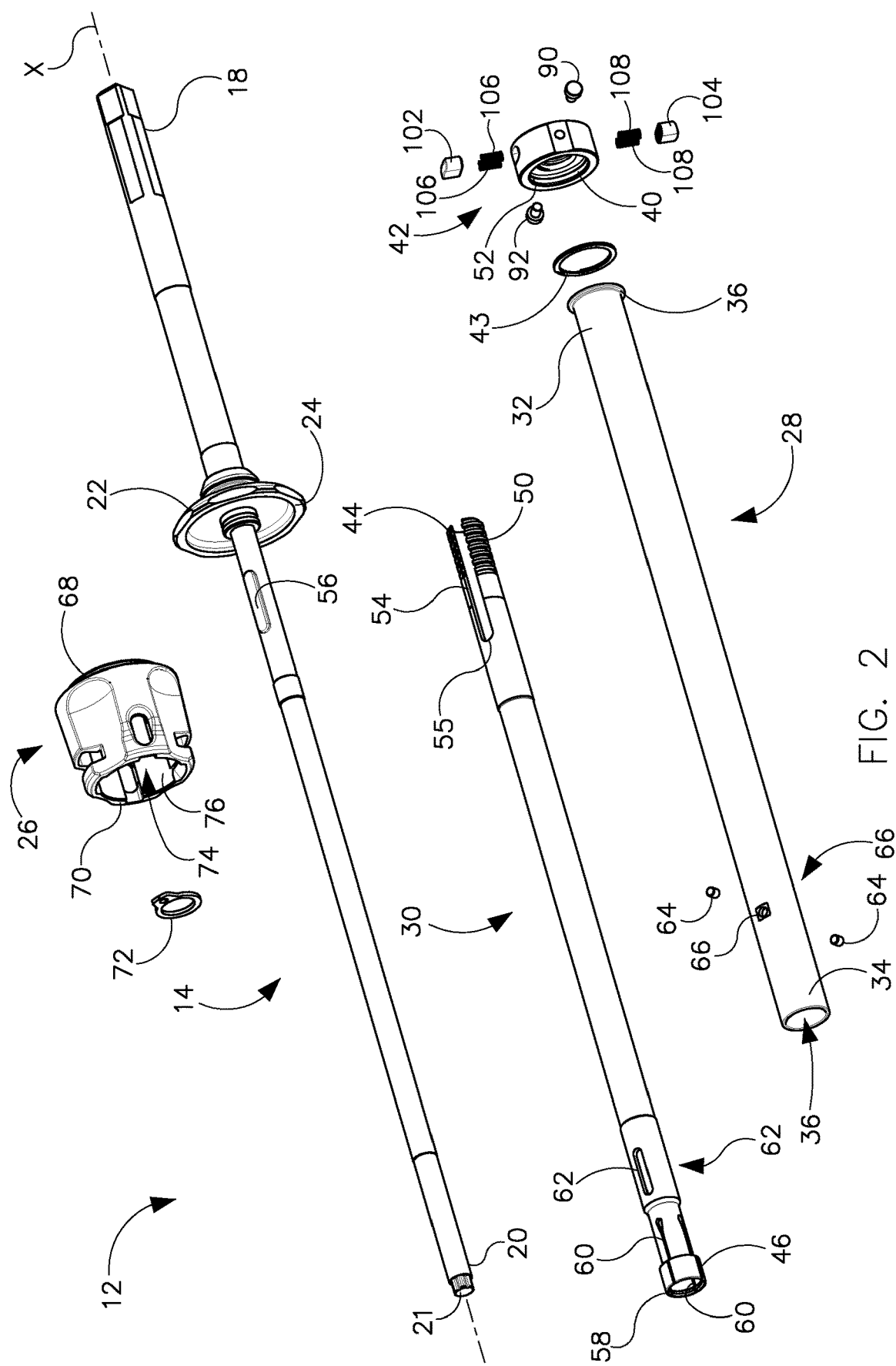
FIG. 2 is a perspective view with parts separated of the components of the surgical system shown in FIG. 1.
Figure 4:
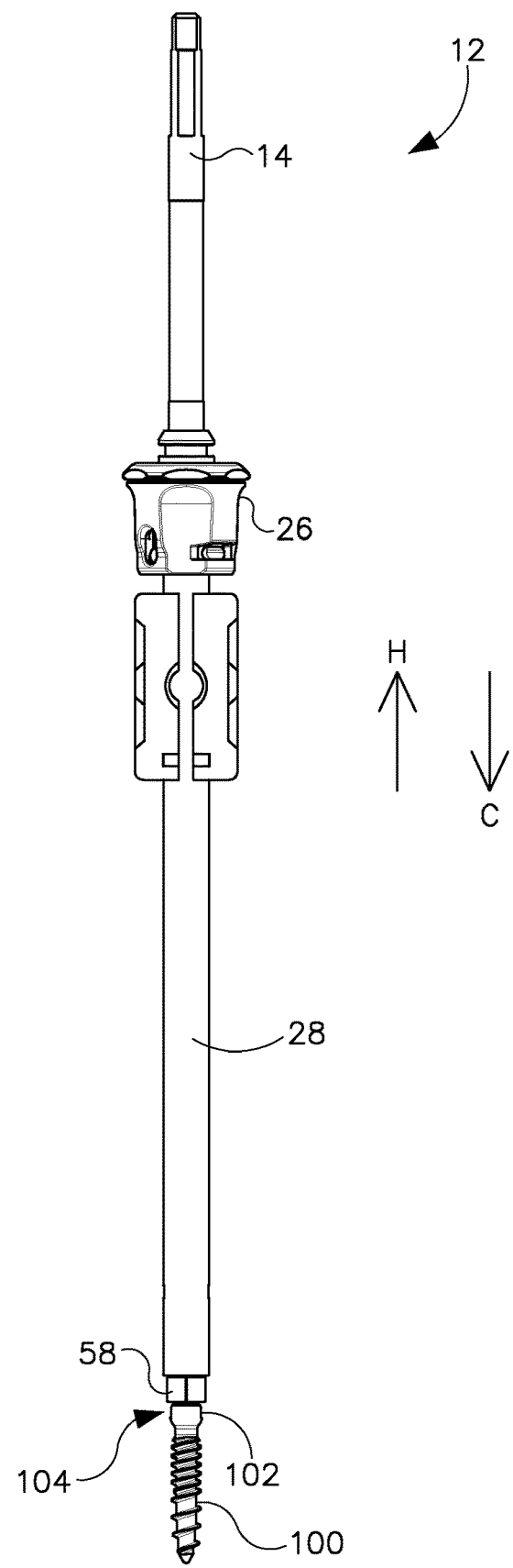
FIG. 4 is a side view of components of the surgical system shown in FIG. 1.

Spinal implant system 10 includes a surgical instrument, for example, a surgical driver 12. Surgical driver 12 is configured for connection with an implant, for example, a bone fastener 300, as shown in FIG. 1. Surgical driver 12 includes a member, for example, an inner shaft 14. Shaft 14 is configured for engagement with a member, for example, an inner sleeve 30, as described herein. Shaft 14 extends between an end 18 and an end 20 and defines a longitudinal axis X disposed therebetween, as shown FIG. 2. End 18 is configured for engagement with a member, for example, a navigation component 200, as described herein. End 20 includes a drive 21 connectable with a head 302 including a drive socket 304 of bone fastener 300, as shown in FIGS. 2, 4 and 10. Drive 21 includes a star shaped configuration (see, for example, a similar star shaped configuration of Torx® (Acument Global Technologies, Inc., Sterling Heights, Michigan, USA)). In some embodiments, drive 21 may have different cross-section configurations, including square, hexagonal, polygonal, triangular or hexalobe. In some embodiments, end 20 may have various surface configurations, including, smooth, rough, arcuate, undulating, porous, semi-porous, dimpled, polished and/or textured.

Figure 24:
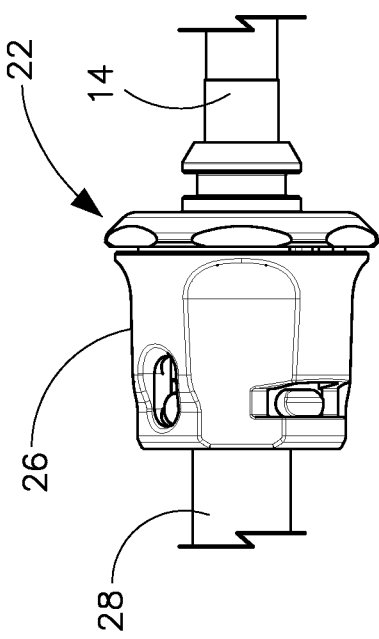
FIG. 24 is a break away view of components of the surgical system shown in FIG. 1.
Figure 25:
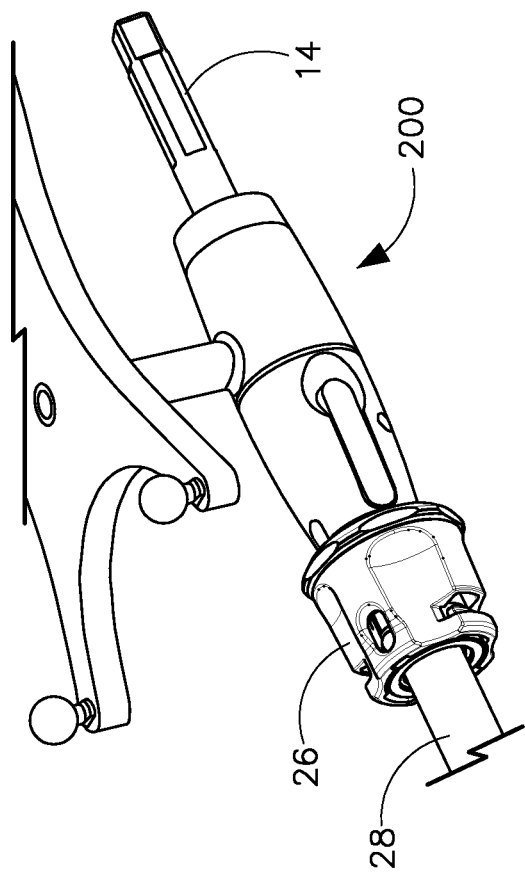
FIG. 25 is a break away view of components of the surgical system shown in FIG. 1.
Figure 23:
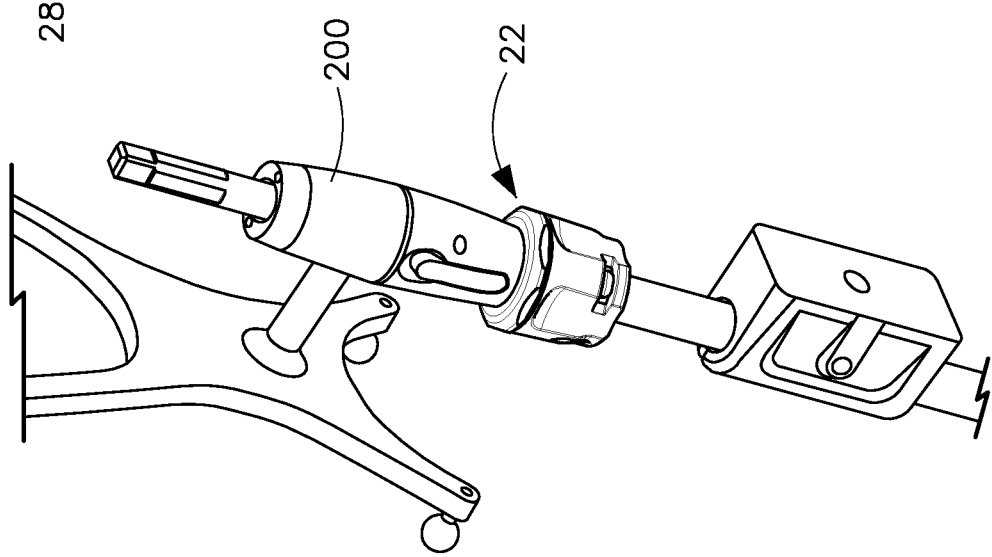
FIG. 23 is a break away view of the components shown in FIG. 1.

Shaft 14 includes a bushing 22, as shown in FIG. 2. Bushing 22 is configured for connection with navigation component 200. Bushing 22 is press fit welded to a surface of shaft 14. Bushing 22 includes a flange 24 configured for engagement with a component of an actuator 25, for example, a knob 26, as shown in FIGS. 2 and 24, and described herein. Flange 24 is configured to contact a surface of knob 26. In some embodiments, flange 24 is configured to prevent loosening of knob 26 during use.

Surgical driver 12 includes a member, for example, an outer sleeve 28, as shown in FIG. 2. Outer sleeve 28 is configured for releasable connection to and translation, for example, axial translation within knob 26. In some embodiments, outer sleeve 28 is configured for releasable connection with variously configured drivers and is not limited to connection with surgical driver 12. Outer sleeve 28 extends between an end 32 and an end 34. In some embodiments, outer sleeve 28 may have alternate cross section configurations, for example, oval, oblong, square, polygonal, irregular, uniform, non-uniform, offset, staggered, undulating, arcuate, variable and/or tapered. In some embodiments, outer sleeve 28 may have various surface configurations, for example, smooth, rough, arcuate, undulating, porous, semi-porous, dimpled, polished and/or textured.

Outer sleeve 28 includes an inner surface that defines a passageway 36 that is coaxial with longitudinal axis X and is configured for disposal of inner sleeve 30, as described herein. In some embodiments, passageway 36 may have various surface configurations, for example, smooth, rough, arcuate, undulating, porous, semi-porous, dimpled, polished and/or textured.

End 32 includes a surface that defines a rim 38, as shown in FIGS. 2 and 6. Rim 38 is configured for engagement with an interior groove 40 of a component of actuator 25, for example, an adjustment collar 42 and a retaining ring 43. Engagement between adjustment collar 42 and outer sleeve 28 facilitates translation of outer sleeve 28 within knob 26, as described herein. Rim 38 is rotatably fixed with adjustment collar 42, as described herein. In some embodiments, rim 38 may have various surface configurations, for example, smooth, rough, arcuate, undulating, porous, semi-porous, dimpled, polished and/or textured.

Inner sleeve 30 extends between an end 44 and an end 46, as shown in FIG. 2. Inner sleeve 30 is configured for disposal with outer sleeve 28 and engagement with shaft 14. In some embodiments, inner sleeve 30 may have alternate cross section configurations, for example, oval, oblong, triangular, square, polygonal, irregular, uniform, non-uniform, offset, staggered, undulating, arcuate, variable and/or tapered. In some embodiments, inner sleeve 30 may have alternate surface configurations, for example, smooth, rough, arcuate, undulating, porous, semi-porous, dimpled, polished and/or textured.

Figure 8:
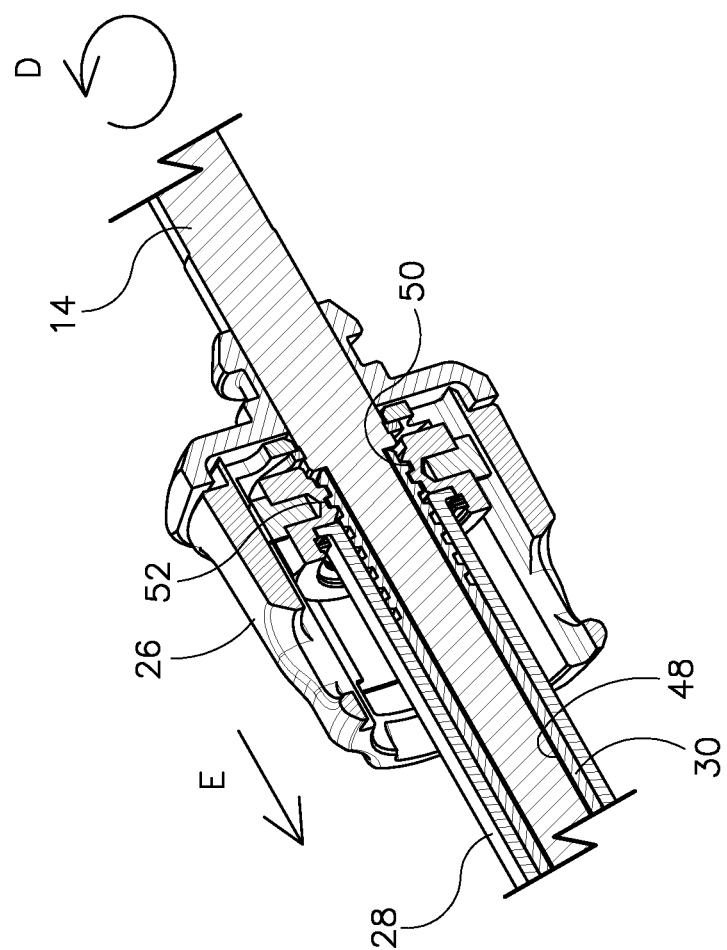
FIG. 8 is a cross section view of the components shown in FIG. 7.
Figure 7:
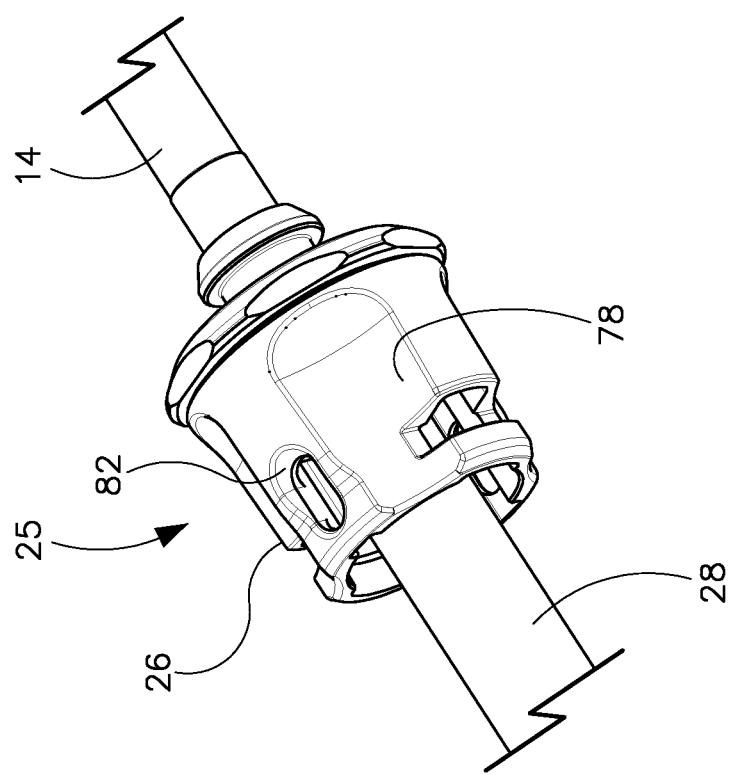
FIG. 7 is a break away view of components of the surgical system shown in FIG. 1.
Figure 12:
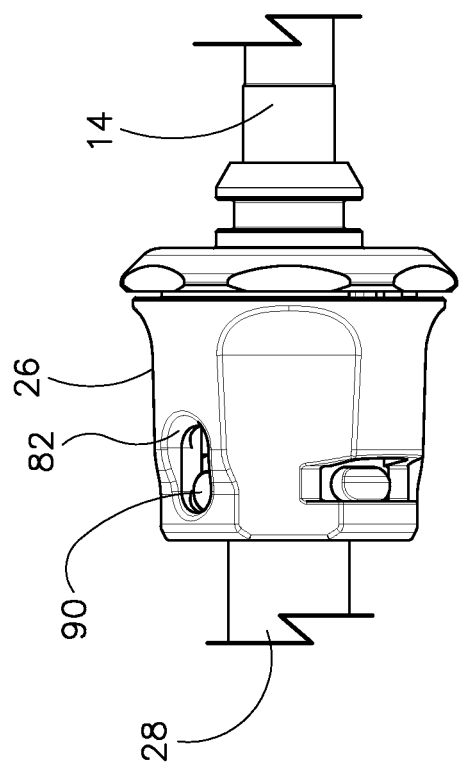
FIG. 12 is a break away view of components of the surgical system shown in FIG. 1.
Figure 13:
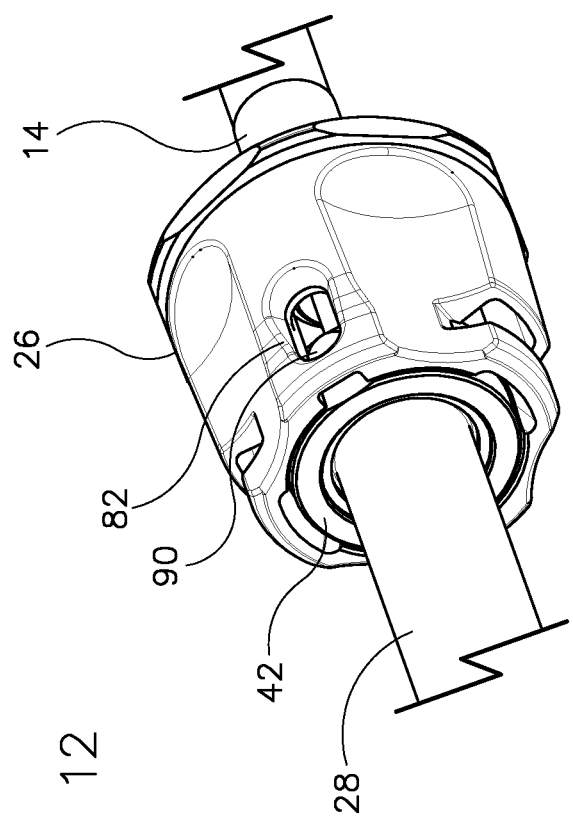
FIG. 13 is a break away view of components of the surgical system shown in FIG. 1.
Figure 11:
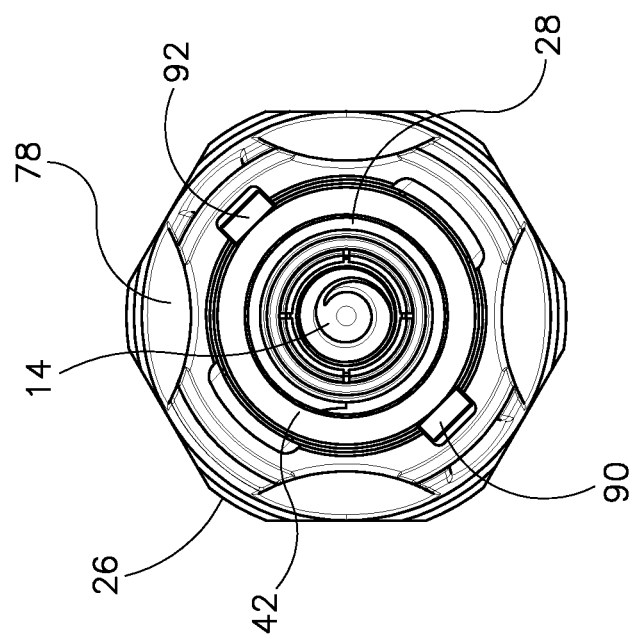
FIG. 11 is an end view of components of the surgical system shown in FIG. 1.

Inner sleeve 30 includes an inner surface that defines a passageway 48, as shown in FIG. 8. Passageway 48 is coaxial with longitudinal axis X and is configured for engagement with shaft 14, as described herein. In some embodiments, passageway 48 may have various surface configurations, for example, smooth, rough, arcuate, undulating, porous, semi-porous, dimpled, polished and/or textured.

End 44 includes a threaded surface 50, as shown in FIG. 2. Threaded surface 50 is configured for engagement with a threaded inner surface 52 of adjustment collar 42 such that inner sleeve 30 translates relative to adjustment collar 42, as shown in FIGS. 2 and 8. In some embodiments, threaded inner surface 52 may have alternative surface configurations, for example, smooth, rough, arcuate, undulating, porous, semi-porous, dimpled, polished and/or textured. End 44 includes a surface that includes a slot, for example, a keyway 54, as shown in FIG. 2. Keyway 54 is configured for engagement with a projection or tab, for example, a key 56 of shaft 14 such that shaft 14 matingly engages with inner sleeve 30. Keyway 54 includes an end 55 configured to limit translation of key 56 of shaft 14 during engagement of key 56 with end 55. In some embodiments, keyway 54 may have alternately shaped configurations, for example, oval, oblong, triangular, square, polygonal, irregular, uniform, non-uniform, offset, staggered, undulating, arcuate, variable and/or tapered. In some embodiments, key 56 may have alternately shaped configurations that match the shaped configuration of keyway 54, for example, oval, oblong, triangular, square, polygonal, irregular, uniform, non-uniform, offset, staggered, undulating, arcuate, variable and/or tapered.

Figure 3:
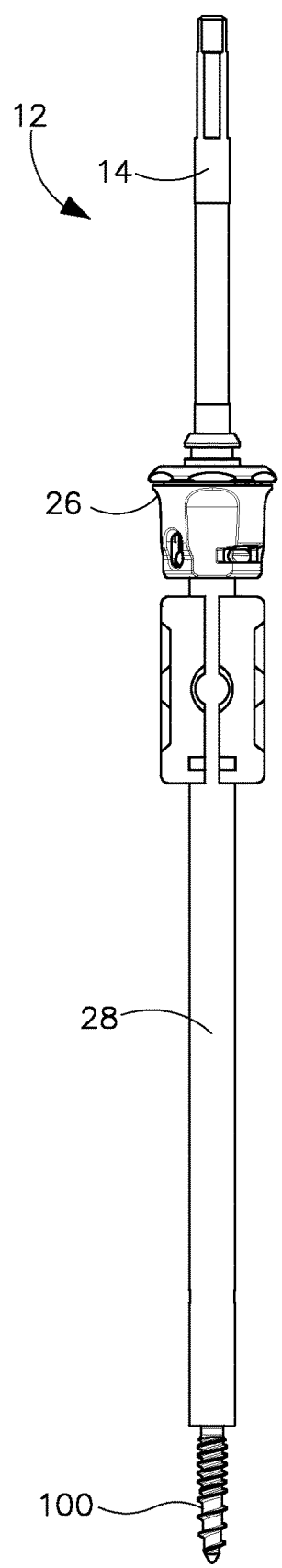
FIG. 3 is a side view of components of the surgical system shown in FIG. 1.

End 46 includes a collet 58, as shown in FIGS. 2, 4 and 10. Collet 58 is configured for connection with bone fastener 300, for example, with a correspondingly shaped outer surface of head 302, as shown in FIGS. 4 and 10. Collet 58 includes a plurality of circumferential slots 60 such that collet 58 is flexible or can flexibly engage head 302. Collet 58 is flexible such that collet 58 expands about head 302 and contracts about head 302 to connect head 302 with sleeve 30. Collet 58 is configured for engagement with end 34 of outer sleeve 28, as shown in FIGS. 3 and 4. Collet 58 expands about head 302 when collet 58 is not engaged with end 34 of outer sleeve 28, as shown in FIG. 4, and collet 58 contracts about head 302 when engaged with end 34 of outer sleeve 28, as shown in FIG. 3. Engagement between end 34 of outer sleeve 28 with collet 58 tensions collet 58 such that collet 58 contracts about head 302. In some embodiments, collet 58 includes various cross section configurations, for example, round for mating engagement with the correspondingly shaped outer surface of head 302. In some embodiments, collet 58 may have alternative surface configurations, for example, smooth, rough, arcuate, undulating, porous, semi-porous, dimpled, polished and/or textured.

Inner sleeve 30 includes a surface that defines a pair of slots 62, as shown in FIG. 2. Slots 62 are disposed adjacent collet 58 and are configured for slidable engagement with a pair of pins 64 disposed within a pair of openings 66 defined from a surface of outer sleeve 28. Outer sleeve 28 is translatable relative to inner sleeve 30, and inner sleeve 30 is rotatably fixed relative to outer sleeve 28 via engagement of slots 62, pins 64 and openings 66. In some embodiments, slots 62 may have alternate cross section configurations, for example, oval, oblong, triangular, square, polygonal, irregular, uniform, non-uniform, offset, staggered, undulating, arcuate, variable and/or tapered.

Knob 26 extends between an end 68 and an end 70, as shown in FIG. 2. See, for example, the embodiments and disclosure of systems and methods of components of an actuator, shown and described in commonly owned and assigned U.S. patent application Ser. No. 17/527,491 filed Nov. 16, 2021, and published as U.S. Patent Application Publication No. US 2023-0149056 A1, on May 18, 2023, the entire contents of which being incorporated herein by reference.

A retaining ring 72 is configured for disposal at end 68. Retaining ring 72 is configured for engagement with a portion of shaft 14 and an inner surface of bushing 22, as shown in FIG. 6, such that knob 26 is translationally fixed with retaining ring 72 and flange 24 but is configured to rotate relative to shaft 14. Knob 26 is releasably connectable with outer sleeve 28 via adjustment collar 42, and outer sleeve 28 is translatable relative to knob 26 via adjustment collar 42, as described herein. Knob 26 defines a cavity 74. An interior wall 76 of knob 26 is configured for slidable engagement with an outer surface of adjustment collar 42, as shown in FIG. 6. In some embodiments, cavity 74 may have alternate cross section configurations, for example, oval, oblong, triangular, square, polygonal, irregular, uniform, non-uniform, offset, staggered, undulating, arcuate, variable and/or tapered.

Knob 26 defines an exterior gripping surface 76 that includes at least one indent 78, as shown in FIG. 5. In some embodiments, gripping surface 76 may have alternative surface configurations, for example, smooth, rough, arcuate, undulating, porous, semi-porous, dimpled, polished and/or textured.

Knob 26 includes a wall 80 that defines a pair of opposing windows 82, as shown in FIGS. 5, 6, 9 and 10. Windows 82 are configured to display indicia, for example, pins 90, 92 of adjustment collar 42 to indicate translation/positioning of outer sleeve 28 relative to knob 26, as described herein. Wall 82 includes inner surfaces 84, as shown in FIG. 10. Inner surfaces 84 are tapered. In some embodiments, inner surfaces 84 are tapered to increase visibility of pins 90, 92. In some embodiments, windows 82 may have alternate cross section configurations, for example, oval, oblong, triangular, square, polygonal, irregular, uniform, non-uniform, offset, staggered, undulating, arcuate, variable and/or tapered.

Adjustment collar 42 is configured to releasably connect and translate outer sleeve 28 with knob 26, as described herein. Translation of outer sleeve 28 within knob 26 via adjustment collar 42 enables the bucket length of surgical driver 12, described herein, to be shortened. In some embodiments, surgical driver 12 includes a bucket length range of 201 mm to 260 mm and is compatible for connection with bone fastener 300 lengths of 25 to 150 mm. Adjustment collar 42 includes a surface that defines a recess 86 and a recess 88, as shown in FIGS. 14 and 15. Recess 86 is disposed opposite of recess 88. Pin 90 is configured for fixed engagement with recess 86 and pin 92 is configured for fixed engagement with recess 88. Pin 90 is configured for slidable engagement with an interior slot 94 of wall 76 of knob 26 and pin 92 is configured for slidable engagement with an interior slot 96 of wall 76 of knob 26 for translation of adjustment collar 42 within knob 26, as shown in FIG. 16. Pins 90, 92 are translated within slots 94, 96 respectively and during selected translation of outer sleeve 28, pins 90, 92 are viewable via windows 82 of knob 26, as shown in FIG. 19. In some embodiments, pins 90, 92 are laser welded to recesses 86, 88. In some embodiments, all or a portion of pins 90, 92 are laser marked a selected color, for example, black. In some embodiments, pins 90, 92 are manufactured in one or more selected colors, for example, pink, red, orange, yellow, green, blue, purple, brown, white and/or black. In some embodiments, pins 90, 92 are anodized and/or PVD coated.

Adjustment collar 42 includes a surface that defines a recess 98 and a recess 100, as shown in FIG. 15. Recess 98 is disposed opposite of recess 100. A button 102 is configured for disposal with recess 98 and a button 104 is configured for disposal with recess 100, as shown in FIGS. 14 and 15. Buttons 102, 104 are configured to prevent axial translation of outer sleeve 28 relative to knob 26 and to facilitate disengagement of outer sleeve 28 with knob 26. Button 102 is biased, for example, via a pair of springs 106 and button 104 is biased, for example, via a pair of springs 108, as shown in FIG. 15. In some embodiments, springs 106 and 108 include a force of 1 to 4 lbs when contracted. Button 102 is configured for slidable engagement with an interior slot 110 of wall 76 of knob 26 and button 104 is configured for slidable engagement with an interior slot 112 of wall 76 of knob 26, as shown in FIG. 16. Buttons 102, 104 are translated within slots 110, 112 respectively to dispose buttons 102, 104 with transverse openings 114, 116 respectively of knob 26, as shown in FIGS. 16 and 19. Buttons 102, 104 are configured for snap engagement with openings 114, 116, as shown in FIG. 18. Pins 117 are configured to retain buttons 102, 104 with adjustment collar 42, as shown in FIG. 14. In some embodiments, buttons 102, 104 include plungers.

Adjustment collar 42 includes a cavity 118, as shown in FIG. 14. Inner sleeve 30 is configured for disposal within cavity 118. An interior wall 115 of adjustment collar 42, as shown in FIG. 14 includes interior groove 40 that engages rim 38 of outer sleeve 28 and threaded inner surface 52 that engages with threaded surface 50 of inner sleeve 30, as described herein. In some embodiments, wall 115 may have alternative surface configurations, for example, smooth, rough, arcuate, undulating, porous, semi-porous, dimpled, polished and/or textured.

Bone fastener 300 includes head 302 including drive socket 304 configured for engagement with shaft 14 and an elongated shaft 306 configured for penetrating tissue, as shown in FIGS. 9 and 10. In some embodiments, selected portions or all of bone fastener 300 may have various cross-section configurations, for example, oval, oblong, triangular, rectangular, square, polygonal, irregular, uniform, non-uniform, variable, tubular and/or tapered. In some embodiments, selected portions or all of bone fastener 300 may have various surface configurations, for example, smooth and/or surface configurations to enhance engagement with tissue, for example, rough, arcuate, undulating, porous, semi-porous, dimpled, polished and/or textured.

Shaft 306 has a cylindrical cross section configuration and includes an outer surface having an external thread form. In some embodiments, the thread form may include a single thread turn or a plurality of discrete threads. In some embodiments, other engaging structures may be disposed on shaft 306, for example, a nail configuration, barbs, expanding elements, raised elements and/or spikes to facilitate engagement of shaft 306 with tissue, for example, vertebrae.

In some embodiments, the outer surface of shaft 306 may include one or a plurality of openings. In some embodiments, all or only a portion of shaft 306 may be disposed at alternate orientations, relative to a longitudinal axis of bone fastener 300, for example, transverse, perpendicular and/or other angular orientations such as acute or obtuse, co-axial and/or may be offset or staggered. In some embodiments, all or only a portion of shaft 306 may be cannulated.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In some embodiments, spinal implant system 10 is employed with an end effector 202, as shown in FIG. 1 of a robotic arm (not shown) to facilitate implantation with the robotic arm. In some embodiments, spinal implant system 10 is employed with robotic and/or navigation guidance (including navigation component 200), which may include an image guide.

Surgical driver 12 is assembled prior to the surgical procedure. To releasably connect outer sleeve 28 with knob 26, adjustment collar 42 attached to outer sleeve 28 and inner sleeve 30 is translated, in a direction shown by arrow A in FIG. 5. Adjustment collar 42 engages wall 76 of knob 26, as shown in FIG. 6. Pins 90, 92 slidably engage slots 94, 96 and buttons 102, 104 are depressed and engage with slots 110, 112. Buttons 102, 104 are disposed with openings 114, 116 as springs 106, 108 expand to translate buttons 102, 104 in an upward direction, as shown by arrows B in FIG. 19, in a snap fit engagement of buttons 102, 104 with openings 114, 116 thereby releasably connecting outer sleeve 28 with knob 26.

To connect surgical driver 12 with bone fastener 300, drive 21 engages with socket 304 of bone fastener 300. Shaft 14 is held rigid by a user and inner sleeve 30 is translated in a direction, for example, a distal direction, as shown by arrow C in FIG. 4 to engage collet 58 with head 302. Knob 26 is rotated in a direction, as shown by arrow D in FIG. 8 to translate outer sleeve 28 in a direction, for example, a distal direction, as shown by arrow E in FIGS. 8 and 9 to translate end 34 of outer sleeve 28 over collet 58. Translation of end 34 of outer sleeve 28 over collet 58 facilitates contraction of collet 58 about head 302 to connect surgical driver 12 with bone fastener 300. Shaft 14 engages socket 304 to drive and fix bone fastener 300 with tissue, for example, a vertebra V1 of vertebrae V, shown in FIG. 1.

To disconnect bone fastener 300 from surgical driver 12, knob 26 is rotated in a direction, shown by arrow F in FIG. 6. Outer sleeve 28 is translated in a direction, for example, a proximal direction, as shown by arrow G in FIGS. 6 and 10 via rotation of knob 26 until collet 58 is fully exposed. Shaft 14 and collet 58 are pulled in a direction, for example, a proximal direction, as shown by arrow H in FIG. 4 to disengage socket 304 and head 302 of bone fastener 300 respectively.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal implant system 10 are removed from the surgical site and the incision is closed.

To disassemble/disconnect outer sleeve 28 from knob 26, buttons 102, 104 are simultaneously translated in a downward direction, as shown by arrows I in FIG. 19. Buttons 102, 104 are translated into slots 110, 112 as outer sleeve 28 is disconnected from knob 26 and translated in a direction, as shown by arrow J in FIG. 5.

One or more of the components of spinal implant system 10 can be made of radiolucent materials such as polymers. Radiomarkers may be included for identification under x-ray, fluoroscopy, CT or other imaging techniques. In some embodiments, surgical driver 12 is guided to the surgical site via a guidewire, for example, a K-wire (not shown) and/or without the use of an image guide, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument comprising:
a first member;
a second member disposable with the first member and including an inner surface;
an actuator comprising a knob and a collar, the collar being positioned in a cavity of the knob, the collar being releasably connectable with the first member; and
a third member being engageable with the inner surface, the first member and the second member being translatable relative to the knob,
wherein the knob includes a wall including at least one slot and at least one window, and wherein the collar includes at least one pin engageable with the at least one slot and viewable within the at least one window.

2. A surgical instrument as recited in claim 1, wherein the first member extends between opposite proximal and distal surfaces, the collar being engageable with the proximal surface.

3. A surgical instrument as recited in claim 1, wherein the collar is slidably engageable with the wall.

4. A surgical instrument as recited in claim 3, wherein the knob is spaced apart from the first member by the collar.

5. A surgical instrument as recited in claim 1, wherein the wall includes inner surfaces that are tapered.

6. A surgical instrument as recited in claim 1, wherein the at least one slot is slidably engageable with the at least one pin to translate the collar within the knob.

7. A surgical instrument as recited in claim 1, wherein the wall includes at least one opening that is spaced apart from the at least one slot.

8. A surgical instrument as recited in claim 7, wherein the collar includes at least one biased button, the at least one button being engageable with the at least one slot and configured for disposal with the at least one opening.

9. A surgical instrument as recited in claim 8, wherein the at least one button is disposable with the at least one opening via a snap engagement.

10. A surgical instrument as recited in claim 8, wherein the at least one button is disposable with the at least one opening to fix the collar with the knob.

11. A surgical instrument as recited in claim 1, wherein the second member includes an inner sleeve including a collet connectable with a bone fastener head.

12. A surgical instrument as recited in claim 11, wherein the bone fastener head includes a drive socket and the third member includes an inner shaft having a drive connectable with the drive socket.

13. A surgical instrument comprising:
a first member;
a second member disposable with the first member and including an inner surface;
an actuator comprising a knob and a collar, the collar being positioned in a cavity of the knob, the collar being releasably connectable with the first member; and
a third member being engageable with the inner surface, the first member and the second member being translatable relative to the knob,
wherein the knob includes a wall including at least one slot and at least one opening, and
wherein the collar includes at least one biased button, the at least one button being engageable with the at least one slot and configured for disposal with the at least one opening.

14. A surgical instrument as recited in claim 13, wherein the at least one button is disposable with the at least one opening via a snap engagement.

15. A surgical instrument as recited in claim 13, wherein the at least one button is disposable with the at least one opening to fix the collar with the knob.

16. A surgical instrument as recited in claim 13, wherein the first member extends between opposite proximal and distal surfaces, the collar being engageable with the proximal surface.

17. A surgical instrument as recited in claim 13, wherein the collar is slidably engageable with the wall.

18. A surgical instrument as recited in claim 17, wherein the knob is spaced apart from the first member by the collar.

19. A surgical instrument as recited in claim 13, wherein the wall includes inner surfaces that are tapered.

20. A surgical instrument as recited in claim 13, wherein the second member includes an inner sleeve including a collet connectable with a bone fastener head.

\* \* \* \* \*